United States Patent [19]

Sarnoff et al.

[11] 4,433,684

[45] Feb. 28, 1984

[54] ASSEMBLY FOR ADMINISTERING RESPIRATORY MEDICAMENT DOSAGE THROUGH A GAS MASK

[75] Inventors: Stanley J. Sarnoff, Bethesda, Md.; Rudolph S. Malooley, Annandale, Va.; George B. Calkins; William R. Tarello, both of Bethesda, Md.

[73] Assignee: Survival Technology, Inc., Bethesda, Md.

[21] Appl. No.: 244,913

[22] Filed: Mar. 18, 1981

[51] Int. Cl.³ .............................................. A61M 15/00
[52] U.S. Cl. ........................... 128/203.21; 128/203.29; 128/202.15; 128/206.17
[58] Field of Search ...................... 128/202.15, 202.13, 128/203.15, 200.23, 272.3, 205.24, 205.21, 203.21, 203.12, 203.29, 206.17; 222/402.2, 402.14; 141/67

[56] References Cited

U.S. PATENT DOCUMENTS

| 1,366,437 | 1/1921 | Wagenhorst | 128/202.15 |
| 1,903,831 | 4/1933 | Monro | 128/202.15 |
| 2,549,303 | 4/1951 | Friden | 128/203.15 |
| 2,968,427 | 1/1961 | Meshberg | 222/394 |
| 3,490,452 | 1/1970 | Greenfield | 128/200.23 |
| 4,325,496 | 4/1982 | Malpas | 128/272.3 |

FOREIGN PATENT DOCUMENTS

| 1274888 | 8/1968 | Fed. Rep. of Germany | 128/202.15 |
| 2040980 | 2/1972 | Fed. Rep. of Germany | 128/202.15 |

*Primary Examiner*—Henry J. Recla
*Attorney, Agent, or Firm*—Cushman, Darby & Cushman

[57] ABSTRACT

An assembly for enabling a respiratory medicament to be administered to a gas mask wearer without breaking the seal between the face blank of the gas mask and the wearer's face. The assembly comprises a container, a respiratory medicament dosage releasably disposed within the container, and a shroud covering the container for (1) interiorly communicating with the exterior of a normally closed passage extending through the face blank of the gas mask to the sealed interior thereof, (2) exteriorly isolating the container and (3) enabling the respiratory medicament dosage to be released from the container while the interior communicating and exterior isolating relationships are maintained.

4 Claims, 4 Drawing Figures

ASSEMBLY FOR ADMINISTERING RESPIRATORY MEDICAMENT DOSAGE THROUGH A GAS MASK

This invention relates to personnel survival in a chemical warfare environment and more particularly to improvements in gas mask devices for enabling persons subject to a nerve gas attack to effect respiratory medical treatment of initial symptoms of nerve gas exposure while maintaining a gas mask in operatively sealed relation with the face.

The current gas mask device available to U.S. military personnel is identified as the M17. Its basic component is a face blank which must be brought into peripherally sealed relation with the face of the wearer and maintained therein during operation. The face blank is provided with suitable eyelens to enable the wearer to see while the face blank is sealed in operative relation, suitable filtered inlet and outlet valving to enable the wearer to breathe while the face blank is in sealed operative relation, and a voicemitter to enable the wearer to speak distinctly to others while the face blank is in sealed operative relation. A variation of the M17, identified as the M17A1, incorporates an additional function in the face blank in the form of a drinking tube, which enables the wearer to drink water and other liquids while the face blank is in sealed operative relation. The more recently developed face mask devices, such as the experimental M30, also provide the liquid intake function in addition to the usual sight, breathing and voice transmitting functions.

It is fundamental in the use of all gas masks that initial operation requires the wearer to establish an airtight peripheral seal of the face blank with the wearer's face. It is also fundamental that once this seal is established it should be continuously maintained and never broken. One of the initial symptoms experienced by persons exposed to certain chemical agents as, for example, hydrogen cyanide, is a breathing paralysis or dysfunction. Such breathing difficulties can be overcome if suitable medical treatment (e.g. aspirate amyl nitrite) can be effected in time. Amyl nitrite ampuls in the form of a dosage of amyl nitrite within a breakable container surrounded by gauze are provided military personnel for this purpose, however there is at present no capability enabling this medical treatment to be administered either by oneself or by a buddy while a gas mask is being worn without breaking the seal.

Accordingly it is an object of the present invention to provide an improved gas mask construction which provides the capability of administering respiratory medical treatments such as amyl nitrite and the like while the gas mask is being worn without breaking the operative seal thereof with the wearer's face. In accordance with the principles of the present invention this objective is obtained by enclosing the respiratory medicament dosage within a container and providing a means capable of (1) exteriorly isolating the medicament dosage within the container from a chemical agent environment, (2) interiorly communicating the contained respiratory medicament with the face mask while in sealed operative relation with the wearer's face as through the drinking tube or an adapter on the downstream side of the filter, and (3) releasing the medicament dosage once such interior communication has been established while maintaining such exterior isolation.

In one embodiment of the invention the dosage of the respiratory medicament is an amount constituting a multiple of a single dosage and the container is in the form of a valved respirator of a known type, such as for example, utilized in dispensing a single mist dosage of a respiratory medicament in response to the depression of a discharge tube extending from the container, see for example U.S. Pat. No. 2,968,427. Where a multiple dosage container of the type capable of ejecting successive single dosages is utilized, the dosage tube is enclosed within a shroud capable of being connected to an adapter collar mounted between the filter and the inlet opening of the face blank of the gas mask device. The connection enables the discharge tube to be moved through a rupturable seal in the shroud past a valve in the adapter into an operative position wherein the user is enabled to actuate the container in the usual fashion so that a measured dosage will be ejected into the interior of the adapter in communication with the interior of the face blank downstream from the inlet filter.

In another embodiment of the invention the container and dosage is in the conventional pearl or ampul configuration, the ampul being disposed within a shroud construction capable of cooperatively engaging the end of the drinking tube of the gas mask and operable to enable the user to fracture the ampul and pump the released medicament manually, as by a bellows action, through the drinking tube into the interior of the gas mask device.

Accordingly it is a further object of the present invention to provide an assembly for enabling a respiratory medicament to be administered to a gas mask wearer without breaking the seal between the face blank of the gas mask and the wearer's face, which is simple but effective in operation and economical to produce.

These and other objects of the present invention will become more apparent during the course of the following detailed description and appended claims.

The invention may best be understood with reference to the accompanying drawings, wherein an illustrative embodiment is shown.

Figure 1:
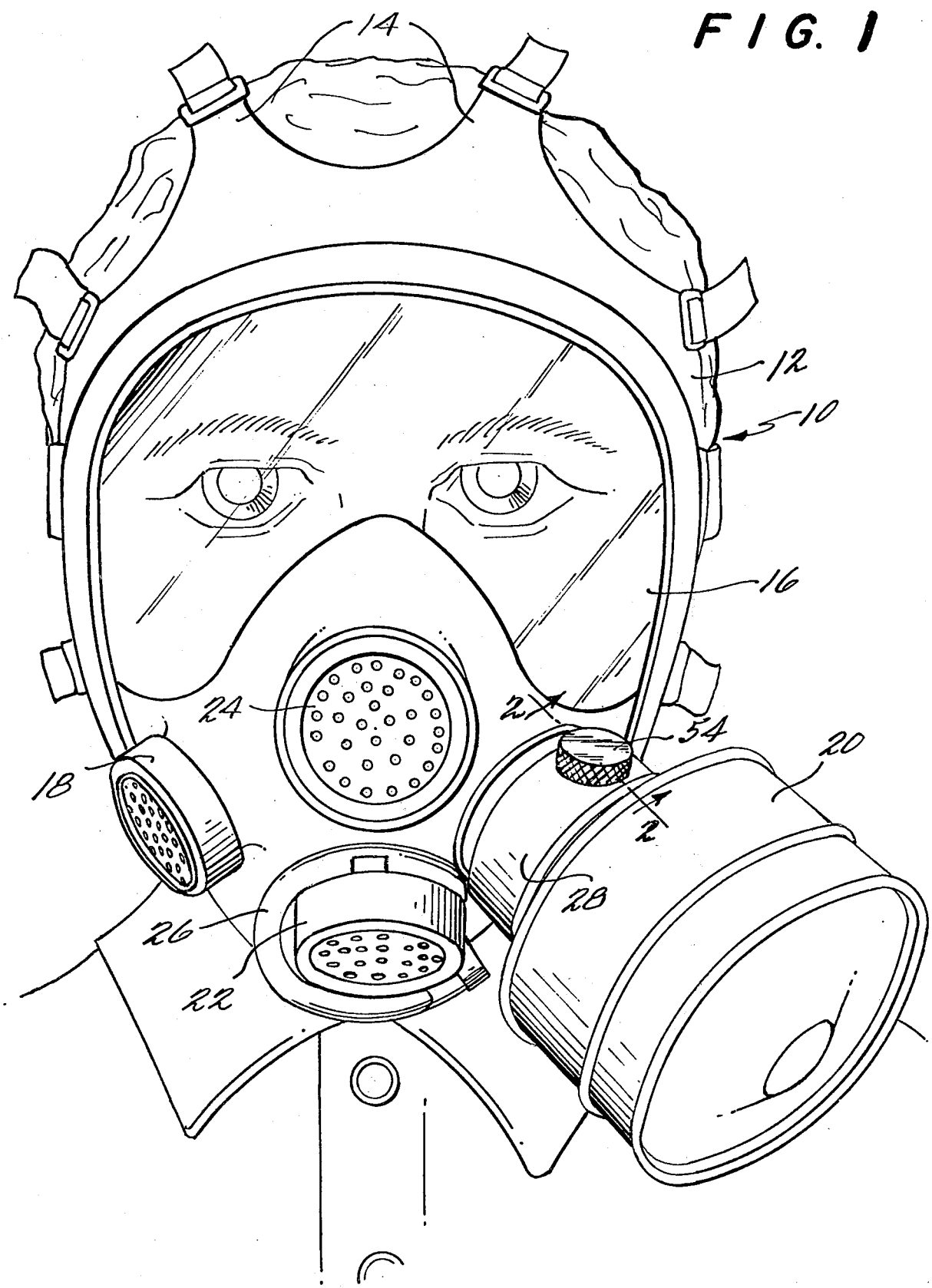
FIG. 1 is a front elevational view of a gas mask of a conventional type having an adapter for communicating with an assembly embodying the principles of the present invention, the adapter being shown with a sealing cap capable of being removed to permit the assembly to be operatively engaged with the adapter.

Referring now more particularly to the drawings, there is shown in FIG. 1 thereof a gas mask 10 which is representative of known configurations as, for example, the M30. It will be understood that the present invention contemplates any known gas mask configuration, such as the M17, the M17A, as well as other known experimental configurations. The mask 10 shown in the drawings includes the usual face blank 12, which is adapted to provide a peripheral seal with the face of the wearer. The face blank 12 is maintained in operative position on the wearer by a head harness 14 which includes a head harness pad (not shown), elastic webbing (not shown), and head harness straps, all in accordance with known technology. Built into the face blank is a clear section 16, enabling the wearer to function visually when wearing the face mask. It will be understood that eyelens may be provided in lieu of the integral clear section 16 as is known.

Formed in opposite sides of the face blank is a pair of inlets, one of which is adapted to be closed, as by a cap 18, and the other of which is adapted to receive a filter can assembly 20. The gas mask 10 also includes a single lower outlet covered by an outlet valve assembly 22. The filter can assembly 20 and valved outlet assembly 22 enable the wearer to breathe functionally. In addition, the gas mask 10 also includes a voicemitter assembly 24 which is also of known construction and provides the wearer with an oral communication function through the face blank.

Finally, the mask 10 includes a drinking tube assembly 26 which is normally retained in a stored condition extending around the outlet valve assembly 22. The drinking tube assembly is adapted to cooperate with a drinking canteen, in accordance with known technology.

Figures 2, 3:
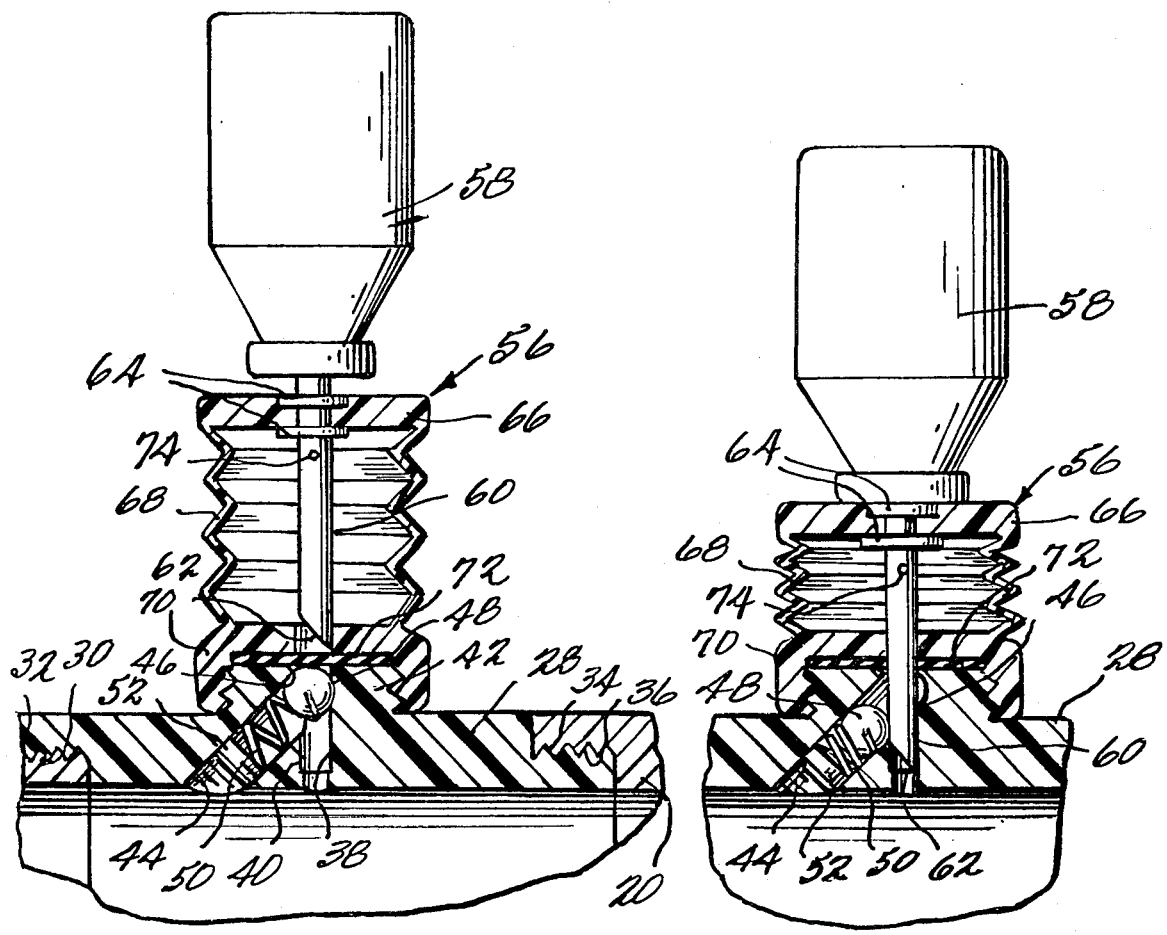
FIG. 2 is an enlarged fragmentary sectional view showing an initial connection between the adapter of FIG. 1 with the cap removed and one form of an assembly embodying the principles of the present invention.
FIG. 3 is a view similar to FIG. 2 showing the assembly in a dosage ejecting position.

In the normal operation of the gas mask 10, filter can assembly 20 is formed with interior female threads for engaging an exterior male thread surrounding either of the inlets. In accordance with the principles of the present invention there is provided instead of the usual direct interconnection as aforesaid, an annular adapter member 28. As best shown in FIG. 2, the adapter member 28 is in the form of a generally cylindrical ring, one end of which is formed with an interior female thread 30 suitable to cooperate with the exterior male thread 32 of the inlet and the other end of which is provided with an exterior male thread 34 suitable to cooperate with the interior female thread 36 of the filter can assembly 20.

The adapter member 28 is formed with a passage 38 extending radially therethrough, the passage being formed with a counterbore so as to define an outwardly facing annular shoulder 40 adjacent the inner end of the passage. Formed on the exterior of the adapter ring in surrounding relation to the exterior end of the passage 38 is an exteriorly threaded annular boss portion 42. The adapter ring member 28 also is formed with an intersecting bore 44 which extends at an angle of approximately 45° from a position spaced axially from the inner end of the passage 38 into a position of intersection therewith at the outer end thereof. The outer end of the bore 44 terminates in a hemispherical seat 46 with which a ball valve 48 is adapted to seat to close off the passage 38. Ball valve 48 is spring urged into a normally closed position by coil spring 50 mounted within bore 44 with its inner end fixed as by a threaded plug 52. It will be understood that the ball valve 48 serves to normally close the passage 38. As best seen in FIG. 1, an added closure in the form of a cap member 54 can be threadedly mounted on the boss portion 42.

When the cap 54 is removed from the threaded portion 42 of the adapter ring 28, the latter is arranged to receive a respiratory medicament administering assembly generally indicated at 56, which is constructed in accordance with the principles of the present invention. The assembly 56 includes a container 58 within which is disposed a respiratory medicament capable of being ejected in successive measured doses as a mist. The container 58 is preferably constructed in accordance with the teachings contained in U.S. Pat. No. 2,968,427, the disclosure of which is hereby incorporated by reference into the present specification. Aerosol containers 58 constructed in accordance with the aforesaid patent are available commercially under the registered trademark MEDIHALER ®, manufactured by Riker Laboratories, Inc. For present purposes it is sufficient to note that the container 58 includes an outlet discharge tube 60 which is mounted so as to be movable into the container to effect the ejection of a measured charge. As shown, the outer extremity of the discharge tube 60 is cut on a bias, as indicated at 62, so as to cooperatively move the ball valve 48 in a manner hereinafter to be more fully described.

The portion of the discharge tube 60 adjacent the container has a pair of mounting rings 64 fixed thereto between which is rotatably sealingly mounted an end wall 66 of a shroud formed of flexible material (e.g. polyethylene) which includes a peripheral wall 68 of bellows configuration extending downwardly from the end wall 66. The lower end of the peripheral wall 68 is connected with an apertured cap portion 70 which is interiorly threaded to engage the exteriorly threaded boss position 42 of the adapter member 28. Mounted within the cap portion 70 is a pierceable diaphragm 72. The flexible shroud initially encompasses the portion of the discharge tube extending outwardly from the mounting rings 64 which include the biased terminal end 62 thereof. It will also be noted that the discharge tube includes a vent opening 74 at a position adjacent the lower mounting ring 64.

In operation, the assembly 56 is mounted on the adapter member 28 as shown in FIG. 2 by simply threadedly engaging the cap portion 70 on the threaded boss portions 42 of the adapter ring. In this regard it will be noted that container 58 may include appropriate indicia which will indicate to the user the proper orientation of the biased extremity 62 of the discharge tube with respect to the ball valve 48. The relative rotational movement provided between the shroud end wall 66 and the mounting rings 64 permits such orientation to be accomplished after the cap portion 70 has been fully secured on the threaded boss portion 42. Once orientation has been achieved in the manner shown in FIG. 2, the end wall 66 is simply pushed downwardly to cause the biased extremity 62 of the discharge tube to pierce through the pierceable diaphragm 72 into engagement with the ball valve 48. The bias of the discharge end 62 causes the ball valve to move from its normal position closing the passageway 38 into an open position, as shown in FIG. 3, permitting the discharge tube to extend into the passageway in communication with the interior of the adapter member. During this movement air trapped in the shroud is vented through the vent hole 74 to the interior of the gas mask. When the extremity 62 engages the shoulder 40, the container 58 is then operable to eject a measured dosage of the respiratory medicament contained therein by simply depressing further on the container itself, which effects a relative inward movement of the discharge tube into the container. In accordance with the teachings of the aforesaid patent, when the container is released the container and tube return to their original position. Successive measured charges can be ejected by successive depressions of the container in the manner aforesaid.

With this arrangement it can be seen that the respiratory medicament dosage is injected into the filtered air stream which is established through the gas mask when the wearer breathes in, thus insuring an effective administration of the dosage to the wearer. It will be understood that the respiratory medicament dosage can be any of the well-known chemical agent antidotes, an exemplary embodiment being amyl nitirite, which is effective as an antidote for hydrogen cyanide.

Figure 4:
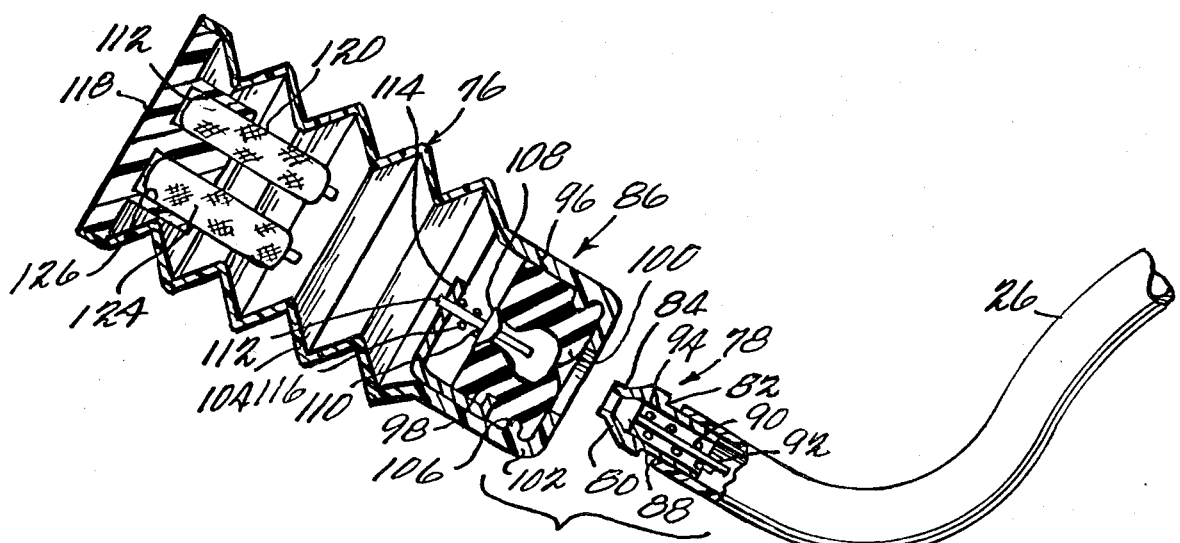
FIG. 4 is a fragmentary sectional view of another form of assembly embodying principles of the present invention illustrating the manner in which the same is adapted to cooperate with the inlet end of the drinking tube of the gas mask.

FIG. 4 illustrates another form of respiratory medicament administering assembly, generally indicated at 76, which is adapted to be used with gas masks which afford the wearer with a drinking function through the provision of a drinking tube 26. FIG. 4 illustrates a typical valved coupling, generally indicated at 78, mounted within the exterior end of the drinking tube 26. As shown, the valved coupling 78 includes a fitting 80 arranged to engage within the end of the tube 26 in sealed relation therewith. The fitting 80 includes a shoulder 82 and a generally frustoconical exterior surface 84 leading thereto enabling the fitting to cooperatively engage a valved coupling 86 forming a part of the medicament administering assembly 76. Valved coupling 78 includes a valve member 88 adapted to engage an internal frustoconical seat provided by the fitting 80 so as to normally close the exterior end of the drinking tube 26. Valve member 88 includes a stem 90 which extends inwardly through a mounting element 92 fixed to the inner end of the fitting 80. A coil spring 94 is disposed in surrounding relation to the valve stem 90 between the valve element 88 and mounting element 92 so as to normally maintain the valve member 88 in its closed position by permitting inward movement of the same into an open position.

Valved coupling 86 of the medicament administering assembly 86 includes a resilient plug member 96 having a cavity 98 formed in the central portion thereof which is closed at its outer end by flexible annular lips 100. The plug member 96, which is formed of resilient material (e.g. rubber), is mounted within the open end portion 102 of a container 104 formed of flexible material as, for example, polyethylene or the like. The plug is retained in position by any suitable means, such as an interior flange 106 engaging within an annular groove in the exterior of the plug. The inner end of the cavity 106 communicates with an interior frustoconical valve seat 108 which is adapted to be engaged by a valve member 110. Valve member 110 includes a stem 112 extending axially therefrom in both directions. The inner end of the valve stem is slidably mounted within a mounting element 114 suitably mounted between the plug 96 and container portion 102. A coil spring 116 is disposed in surrounding relation to the valve stem between the mounting element 114 and valve member 110 so as to normally maintain the valve element 110 in its closed position while permitting movement therefrom into an open position. The peripheral wall of the container 104 is constructed in a bellows configuration and the end portion there opposite from the open end portion 102 is closed, as by a plug 118.

The assembly 76 also includes a measured dosage of the respiratory medicament to be administered, as for example, amyl nitrite, the medicament dosage being packaged in a conventional fracturable ampul 120. The fracturable ampul 120 is disposed within the container so as to be fractured through flexure of the flexible walls thereof, as for example, the peripheral bellows wall 104. To facilitate the fracturing of the ampul 120 the base 110 may have a socket portion 122 formed therein within which to stably receive one end portion of the ampul. With this arrangement the operator need only to push on the bellows-shaped side wall in order to snap open the fracturable container 120.

FIG. 4 also illustrates another feature of the present invention which serves to facilitate the administration of the respiratory medicament such as amyl nitrite released from the fractured ampul 120. This feature includes the provision of a fracturable ampul 124 of ammonia or other respiratory stimulant which, when placed in proximity of the nose or the breathing area of an individual, results in a rapid involuntary sucking in of air by the individual. It will be noted that the ampul 124 may likewise be mounted within a socket 126 in the base 118, the base being provided with suitable indicia to indicate the position of each of the two different ampuls.

The assembly 76 is operated by effectively coupling the valved coupling 78 at the end of the drinking tube 26 with the valved coupling 86 of the assembly 76. In effecting this interengagement it will be noted that the frustoconical exterior surface 84 of the fitting 80 will cause the flexible annular lips 100 to part, permitting the fitting to move within the cavity 106 until the flexible lips engage over the shoulder 82 to retain the same therein. During this movement the outwardly projecting end portion of the valve stem 112 of the valved coupling 86 will engage the end of the valve 88 causing both of the valve members 88 and 110 to be moved from their normally closed positions into their open positions. With the valve members 88 and 110 in their open positions the interior of the container within which the ampuls 120 and 124 are mounted is communicated with interior of the gas mask 10. Ampul 120 is released as aforesaid either prior to the interengagement of the valved couplings, as aforesaid, or after the same has been interengaged, so that the released contents thereof is capable of being communicated with the interior of the gas mask. By engaging the container so as to compress the bellows wall 104 the interior volume of the container is reduced, thereby displacing the contents of the fractured ampul 120 from the interior of the container through the drinking tube 26 into the interior of the gas mask where it can be breathed in by the wearer. Where necessary several pumping actions may be performed on the container to accomplish an effective displacement of an appropriate dosage into the interior of the gas mask through the drinking tube. It will be understood that the capacity or interior size of the container is sufficiently greater than the capacity or interior size of the drinking tube to effect displacement of the air from the container through the drinking tube and into the interior of the gas mask.

Where the assembly 76 includes an ammonia ampul 124 and the condition of the wearer, as determined by his buddy, is such as to warrant the assistance provided by the ammonia ampul, the latter is fractured after the amyl nitrite ampul has been fractured and its contents have been made available to the interior of the gas mask. Once the ammonia ampul is fractured, a pumping action on the container will bring the ammonia into the interior of the gas mask, causing the wearer to involuntarily breathe in with considerable force, thus insuring that the already existing amyl nitrite within the gas mask will be breathed in by the wearer.

It will be understood that the assembly 76 may be simply replaced by new assemblies as additional dosages are required. It will also be understood that the the assembly 76 could be enlarged to accommodate several ampuls of amyl nitrite which could be successively fractured in the same fashion as the two ampuls 120 and 124 described above.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. In a gas mask including a face blank arranged to be peripherally sealed with the wearer's face and a breathing inlet having an exterior filter communicating therewith, the improvement which comprises means including an annular adapter member between said inlet and said filter defining a passage extending radially through said adapter member communicating with the interior of the face blank and exteriorly thereof, said annular member having an exterior threaded portion disposed in surrounding relation with the exterior of said passage, normally closed valve means in said passage, coupling means for sealingly connecting with the passage, a container disposed in sealing relation with said coupling means having a respiratory medicament therein, and means for releasing successive predetermined dosages of said respiratory medicament from said container through said coupling means into the interior of said face blank, said coupling means including a threaded member threadedly engaged with said threaded portion to fixedly secure said threaded member thereto in air excluding sealed relation with respect to the exterior of said passage, a tubular outlet extending from said container in alignment with said passage, flexible shroud means connected with said threaded member and disposed in sealing relation with said tubular outlet, and diaphragm means for providing a seal over said passage, said tubular outlet being adapted to pass through said passage and including means for piercing said diaphragm means and for moving said valve means therein from its normally closed position into an open position.

2. An assembly for use with a gas mask including a face blank arranged to be peripherally sealed with the wearer's face and a breathing inlet having an exterior filter communicating therewith, said assembly comprising means including an annular adapter member between said inlet and said filter defining a passage extending radially through said adapter member communicating with the interior of the face blank and exteriorly thereof, said annular member having an exterior threaded portion disposed in surrounding relation with the exterior of said passage, normally closed valve means in said passage, coupling means for sealingly connecting with the passage, a container disposed in sealing relation with said coupling means having a respiratory medicament therein, and means for releasing successive predetermined dosages of said respiratory medicament from said container through said coupling means into the interior of said face blank, said coupling means including a threaded member threadedly engaged with said threaded portion to fixedly secure said threaded member thereto in air excluding sealed relation with respect to the exterior of said passage, a tubular outlet extending from said container in alignment with said passage, flexible shroud means connected with said threaded member and disposed in sealing relation with said tubular outlet, and diaphragm means for providing a seal over said passage, said tubular outlet being adapted to pass through said passage and including means for piercing said diaphragm means and for moving said valve means therein from its normally closed position to an open position.

3. In a gas mask including a face blank arranged to be peripherally sealed with a wearer's face and means defining a passage communicating with the interior of the face blank and exteriorly thereof, the improvement which comprises a rigid container, a respiratory medicament in said container, an elongated rigid tubular outlet having an outlet end portion mounted in outwardly extending relation with respect to said container for relative movement with respect to said container between an inoperative position and a dosage delivering position, means operable in response to the relative movement of said tubular outlet with respect to said container from said inoperative position to said dosage delivering position for dispensing a dosage of said medicament from said container outwardly through said tubular outlet, a coupling member having an opening of a size to receive said tubular outlet therethrough, diaphragm means sealingly enclosing said opening, flexible shroud means connected with said coupling member and disposed in sealing relation with said tubular outlet so as to define with said coupling member and said diaphragm means an exteriorly sealed space within which the outlet end portion of said tubular outlet is disposed, said outlet end portion including means for piercing said diaphragm means, said coupling member having securing means for fixedly securing the coupling member in air excluding sealed relation with respect to the exterior of said pasage in a position such that said diaphragm means, said opening and said tubular outlet are disposed in aligned relation with said passage so as to enable said tubular outlet to be moved from its sealed position within said space outwardly through said opening in piercing relation to said diaphragm means into said passage in communicating relation with the interior of said face blank so that upon the accomplishment of a relative movement of said tubular outlet with respect to said container from said inoperative position to said dosage delivering position the dosage of medicament dispensed by said dispensing means in response thereto will be communicated with the interior of the face blank for inhalation by the gas mask wearer.

4. An assembly for use with a gas mask, said gas mask including a face blank arranged to be peripherally sealed with a wearer's face and means defining a passage communicating with the interior of the face blank and exteriorly thereof, said assembly comprising a rigid container, a respiratory medicament in said container, an elongated rigid tubular outlet having an outlet end portion mounted in outwardly extending relation with respect to said container for relative movement with respect to said container between an inoperative position and a dosage delivering position, means operable in response to the relative movement of said tubular outlet with respect to said container from said inoperative position to said dosage delivering position for dispensing a dosage of said medicament from said container outwardly through said tubular outlet, a coupling member having an opening of a size to receive said tubular outlet therethrough, diaphragm means sealingly enclosing said opening, flexible shroud means connected with said coupling member and disposed in sealing relation with said tubular outlet so as to define with said coupling member and said diaphragm means an exteriorly sealed space within which the outlet end portion of said tubular outlet is disposed, said outlet end portion including means for piercing said diaphragm means, said coupling member having securing means for fixedly securing the coupling member in air excluding sealed relation with respect to the exterior of said passage in a position such that said diaphragm means, said opening and said tubular outlet are disposed in aligned relation with said passage so as to enable said tubular outlet to be moved from its sealed position within said space outwardly through said opening in piercing relation to said diaphragm means into said passage in communicating relation with the interior of said face blank so that upon the accomplishment of a relative movement of said tubular outlet with respect to said container from said inoperative position to said dosage delivering position the dosage of medicament dispensed by said dispensing means in response thereto will be communicated with the interior of the face blank for inhalation by the gas mask wearer.

* * * * *